(12) United States Patent
Tabata

(10) Patent No.: US 8,771,734 B2
(45) Date of Patent: Jul. 8, 2014

(54) SUSTAINED-RELEASE HYDROGEL PREPARATION

(75) Inventor: Yasuhiko Tabata, Uji (JP)

(73) Assignee: Medgel Corporation, Kyoto-Shi (JP)

( * ) Notice: Subject to any disclaimer, the term of this patent is extended or adjusted under 35 U.S.C. 154(b) by 1596 days.

(21) Appl. No.: 10/549,695

(22) PCT Filed: Mar. 15, 2004

(86) PCT No.: PCT/JP2004/003400
§ 371 (c)(1),
(2), (4) Date: May 26, 2006

(87) PCT Pub. No.: WO2004/082657
PCT Pub. Date: Sep. 30, 2004

(65) Prior Publication Data
US 2006/0251719 A1    Nov. 9, 2006

(30) Foreign Application Priority Data
Mar. 17, 2003   (JP) ................... 2003-071657

(51) Int. Cl.
*A61K 9/22*        (2006.01)
(52) U.S. Cl.
USPC ........................................ 424/468
(58) Field of Classification Search
USPC ........................................ 424/468
See application file for complete search history.

(56) References Cited

U.S. PATENT DOCUMENTS 4,485,088 A * 11/1984 Chvapil ................. 424/447
4,749,574 A *  6/1988 Ueda et al. ............. 424/448
2002/0150605 A1   10/2002 Yui et al.
2004/0253294 A1 * 12/2004 Tabata ................... 424/426
2006/0148691 A1 *  7/2006 Tabata et al. ............ 514/12
2007/0010436 A1 *  1/2007 Tabata et al. ............ 514/12

FOREIGN PATENT DOCUMENTS

| EP | 0 661 045 | 7/1995 |
|---|---|---|
| EP | 1 249 247 A2 | 10/2002 |
| JP | 8-325160 A | 12/1996 |
| JP | 2702729 B2 | 10/1997 |
| JP | 2001-316282 A | 11/2001 |
| JP | 2002-145797 A | 5/2002 |
| WO | WO-99/59549 | 11/1999 |
| WO | WO-00/48576 | 8/2000 |
| WO | WO-02/18450 | 3/2002 |
| WO | WO-03/090805 | 11/2003 |

OTHER PUBLICATIONS

Tabata et al., Protein release from gelatin matrices, Advanced Drug Delivery Reviews, 31 (1998) 287-301.*
Supplementary European Search Report issued Jan. 4, 2010, in European Patent Application No. 04720761.8.
Database WPI Week 200382, Thomson Scientific, London, GB, AN 2003-903372; Abstract corresponding to WO 03/090805 A.

* cited by examiner

*Primary Examiner* — Aradhana Sasan
(74) *Attorney, Agent, or Firm* — Birch, Stewart, Kolasch & Birch, LLP

(57) ABSTRACT

A sustained-release preparation is provided which comprises a drug and a bioabsorbable polymer hydrogel, wherein a concentration gradient of the drug is formed in the hydrogel. Also disclosed is a method of sustained release of a drug in vivo using the sustained-release preparation of the invention. The directionality of the drug release may be controlled by employing the sustained-release preparation of the invention. The sustained-release preparation of the invention is particularly useful as an anti-cancer agent.

14 Claims, 6 Drawing Sheets

SUSTAINED-RELEASE HYDROGEL PREPARATION

TECHNICAL FIELD

The present invention relates to a sustained-release preparation which can control the direction of release of a drug.

BACKGROUND ART

In order to keep a drug concentration constant in a living body for a long period of time, a method of controlling the release by encapsulating the drug in a microcapsule or hydrogel composed of a bioabsorbable polymer which absorbs the drug has been known. Many kinds of natural or synthetic polymers such as collagen, gelatin, polylactic acid, polyglycolic acid and poly-γ-glutamic acid have been reported to be a bioabsorbable polymer which may be used to such an end.

When a sustained-release preparation is embedded into a living body to allow a drug to be released, it is believed to be advantageous also in terms of alleviation of side effects when sustained release of the drug can be realized in a specified direction such as a direction from the embedded site toward the place where the lesion is present, because impairment and damage of peripheral normal tissues resulting from release of the drug toward directions other than the specified direction can be suppressed. However, although a variety of methods have been attempted hitherto in regard to control of the velocity of release, no method has been known allowing control of the direction of release.

Japanese Patent No. 2702729 discloses a sustained-release embedded agent prepared by laminating or adjoining two kinds of matrices, i.e., a matrix obtained by mixing a biodegradable polymer with a biologically active substance, and a matrix comprising a biodegradable polymer alone. The object of this invention is to provide a sustained-release embedding agent enabling control of the velocity of release of a biologically active substance, but control of release directionality is not mentioned.

An object of the present invention is to provide a sustained-release preparation which can control the direction of release of a drug.

DISCLOSURE OF THE INVENTION

The present inventors found that directionality of sustained release can be controlled by producing a sustained-release preparation such that a concentration gradient of a drug is formed in a bioabsorbable polymer hydrogel that releases the drug upon degradation in vivo. Accordingly, an aspect of the invention provides a sustained-release preparation which comprises a drug and a bioabsorbable polymer hydrogel, and is characterized in that a concentration gradient of the drug is formed in the hydrogel. Preferably, the hydrogel is a gelatin hydrogel. Another aspect of the invention provides a method of sustained release of a drug in vivo using a sustained-release preparation which comprises the drug and a bioabsorbable polymer hydrogel, wherein a concentration gradient of the drug is formed in the hydrogel. Preferably, the hydrogel is gelatin hydrogel.

In the sustained-release preparation of the invention, the drug interacts with the bioabsorbable polymer constituting the hydrogel, and therefore it cannot freely disperse in the hydrogel and is not released until the hydrogel itself is degraded and the polymer becomes water-soluble. More specifically, sustained release of the drug is effected upon degradation of the hydrogel, and therefore, formation of the concentration gradient of the drug in the hydrogel causes more drug to be released from the region with higher drug concentration, resulting in sustained release of the drug with directionality.

DETAILED DESCRIPTION OF THE INVENTION

Figure 1:
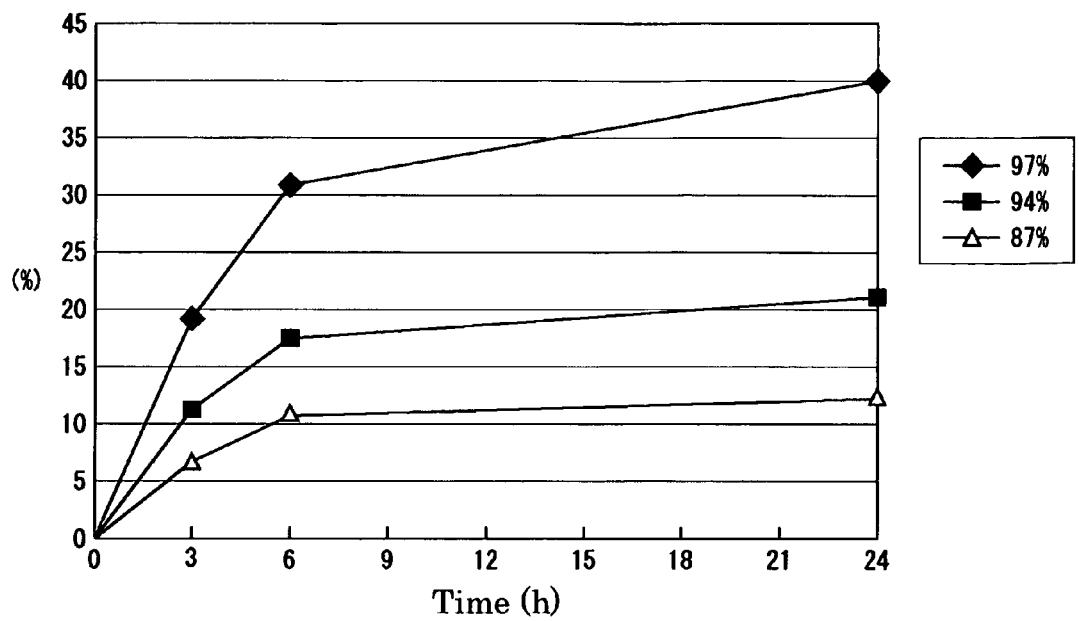
FIG. 1 is a view showing release of CDDP from a CDDP-impregnated hydrogel in vitro.

As used herein, the bioabsorbable polymer used for producing a bioabsorbable polymer hydrogel is a polymer which can form a complex through physicochemical interaction with the drug to effect sustained release, and which will be degraded by hydrolysis and oxygen degradation in vivo, or will be hydrolyzed by an action of a biologically active substance such as an enzyme present in the living body. Specific examples include bioabsorbable synthetic polymers, for example, polysaccharides such as chitin, chitosan, hyaluronic acid, alginic acid, starch and pectin, proteins such as gelatin, collagen, fibrin and albumin, polyamino acids such as poly-γ-glutamic acid, poly-L-lysine and polyarginine, and derivative thereof; or mixtures or chemical conjugates of the compounds described above, and the like. A preferable example is gelatin or a derivative thereof. A derivative as used herein refers to a substance modified to be suitable to form a complex of the drug and the bioabsorbable polymer hydrogel. Specific examples include derivatives having a guanidyl group, a thiol group, an amino group, a carboxyl group, a sulfuric acid group, a phosphoric acid group, or a hydrophobic residue such as an alkyl group, an acyl group or a benzyl group, and a low molecular hydrophobic substance or the like introduced therein. The source of the natural bioabsorbable polymer is not particularly limited, but any one derived from various animals such as humans as well as pigs, cattle, and fishes such as sharks may be used. It may be a naturally occurring polymer, or may be obtained by a fermentation process using a microorganism or a genetic recombinant procedure. Alternatively, it may be produced by chemical synthesis.

As the bioabsorbable polymer, gelatin is preferably used. Gelatin can be obtained by any of various means causing denaturation, such as alkali hydrolysis, acid hydrolysis, oxygen degradation, of collagen that can be collected from any site in a body such as skin, bone or tendon of any variety of animal species including cattle, pig, and fishes, or from any commercially available collagen. Modified gelatin derived from genetic recombinant collagen may be also used.

In order to achieve a more excellent effect to control sustained-release of a drug according to the invention, it is preferable that the bioabsorbable polymer hydrogel is made to be insoluble in water, whereby the release of the drug may be controlled according to the degradation properties of the bioabsorbable polymer hydrogel in vivo. More specifically, the sustained release rate of a drug may be controlled by degradation of the bioabsorbable polymer hydrogel in vivo.

The bioabsorbable polymer hydrogel can be insolubilized by causing formation of a chemical crosslinking between molecules of the bioabsorbable polymer using any of a variety of chemical crosslinking agents. The chemical crosslinking agent may be glutaraldehyde, a water soluble carbodiimide such as EDC, or a condensing agent that forms a chemical bond with propylene oxide, a diepoxy compound, a hydroxyl group, a carboxyl group, an amino group, a thiol group, or an imidazole group. Preferably, the chemical crosslinking agent is glutaraldehyde. In addition, a chemical crosslinkage of the bioabsorbable polymer may also be formed by a thermal dehydrating treatment, ultraviolet rays, gamma rays, or electron rays. These crosslinking treatments may also be used in combination. Furthermore, the hydrogel may also be produced by a physical crosslinkage utilizing a salt crosslinkage, an electrostatic interaction, a hydrogen bond, a hydrophobic interaction or the like.

The degree of crosslinking of the bioabsorbable polymer may be conveniently selected depending on the desired water content, i.e., the level of bioabsorptivity of the hydrogel. When gelatin is used as the bioabsorbable polymer, preferable range of concentration of gelatin is from 1 to 20 w/w % and the crosslinking agent in the hydrogel preparation is from 0.01 to 1 w/w %. Conditions of the crosslinking reaction are not particularly limited, however, the reaction may be carried out, for example, at 0 to 40° C., and preferably 25-30° C., for 1 to 48 hrs, and preferably 12 to 24 hrs. In general, as the concentration of gelatin and the crosslinking agent and crosslinking time are increased, degree of crosslinking of the hydrogel is increased and bioabsorptivity is diminished.

Crosslinking of gelatin can also be conducted by a thermal treatment. Example of crosslinking by a thermal treatment is as follows. An aqueous gelatin solution (preferably approximately 10% by weight) is poured into a plastic dish, followed by air drying to give a gelatin film. The film is allowed to stand under a reduced pressure, preferably at approximately 10 mmHg, generally at 110 to 160° C., and preferably at 120 to 150° C., generally for 1 to 48 hrs, and preferably for 6 to 24 hrs. Alternatively, when a gelatin film is crosslinked by ultraviolet rays, the resulting gelatin film is left under a sterilization lamp usually at room temperature, and preferably at 0 to 40° C. Also, a sponge-like molded product may be obtained by freeze-drying of an aqueous gelatin solution. Crosslinking of the product can be performed similarly by a thermal treatment and ultraviolet rays, gamma rays or electron rays. Alternatively, a combination of the foregoing crosslinking methods may be used.

The shape of the bioabsorbable polymer hydrogel is not particularly limited, but may be in the form of, for example, cylindrical, prismatic, sheet-like, discal, spherical and paste-like. A cylindrical, prismatic, sheet-like or discal shape is particularly suited for use as an embedded chip.

Cylindrical, prismatic, sheet-like or discal gelatin hydrogel can be prepared by adding an aqueous solution of a crosslinking agent to an aqueous gelatin solution, or adding: gelatin to an aqueous solution of a crosslinking agent, then pouring the mixture into a template having a desired shape to allow for crosslinking reaction. Alternatively, an aqueous solution of a crosslinking agent may be added to a molded or a dried gelatin gel. In order to terminate the crosslinking reaction, the mixture may be brought into contact with a low molecular substance having an amino group such as ethanolamine or glycine, or an aqueous solution with pH of not higher than 2.5 may be added. For the purpose of completely eliminating the crosslinking agent and low molecular substances used in the reaction, the thus resulting gelatin hydrogel is washed with distilled water, ethanol, 2-propanol, acetone or the like. The gelatin hydrogel then is used for preparation of the formulation.

The bioabsorbable polymer hydrogel of the invention can be used after cutting into an appropriate size and shape in a conventional manner, followed by freeze-drying and sterilization. The freeze-drying can be carried out by, for example, putting the bioabsorbable polymer hydrogel into distilled water, freeze-drying it in liquid nitrogen for 30 min or more, or at −80° C. for 1 hour or more, and thereafter drying it in a lyophilizer for 1 to 3 days.

Examples of the drug which may be used for producing the sustained-release preparation according to the invention include, for example, antitumor agents, antimicrobial agents, anti-inflammatory agents, antiviral agents, anti-AIDS agents, low molecular drugs such as hormones, bioactive peptides, proteins, glycoproteins, polysaccharides and nucleic acids. Particularly, a drug having a molecular weight of about 10,000 or less is preferred. The drugs may be either a naturally occurring substance or a synthetic products. Examples of particularly preferable drugs include antitumor agents. Among them, platinum based antitumor agents such as cisplatin (CDDP), carboplatin, oxaliplatin, ormaplatin, CI-973 and JM-216 are suited for use in the sustained-release preparation of the invention.

The containing sustained-release bioabsorbable polymer hydrogel preparation of the invention containing a drug can be obtained by, for example, adding the drug solution dropwise to the lyophilized bioabsorbable polymer hydrogel, or soaking the bioabsorbable polymer in the drug solution to allow the drug to impregnate in the hydrogel. To form a concentration gradient of the drug in the bioabsorbable polymer hydrogel, the drug solution may be added dropwise from one face of the bioabsorbable polymer hydrogel in a sheet form, or the bioabsorbable polymer hydrogel may be disposed in an apparatus, such as a diffusion chamber, between cells in which drug solutions having different drug concentration to allow for impregnation of the drug.

Molar ratio of the drug to the bioabsorbable polymer is preferably about 5 or less. More preferably, molar ratio of the drug to the bioabsorbable polymer is from about 5 to about $1/10^4$. The impregnation may be generally conducted at 4 to 37° C. for 15 min to 1 hour, and preferably at 4 to 25° C. for 15 to 30 min. During this time period, the hydrogel is swollen with drug solution, and the drug forms a complex with the bioabsorbable polymer by physicochemical interactions, leading to immobilization of the drug within the bioabsorbable polymerhydrogel. In binding of the drug and the bioabsorbable polymer hydrogel, it is believed that physical interaction such as Coulomb force, hydrogen bonding force and hydrophobic interaction, as well as a coordinate bond between a functional group or a metal on the drug and a functional group on the hydrogel may be involved alone or in conjunction.

In the complex of the drug and the bioabsorbable polymer hydrogel of the invention, the drug incorporated in the complex is gradually released out from the complex as the bioabsorbable polymer hydrogel is degraded in vivo. The release rate is determined by the degree of degradation and absorption of the bioabsorbable polymer hydrogel in vivo, and the extent of strength and stability of the bond between the drug and the bioabsorbable polymer hydrogel in the complex. The degree of degradation and absorption of the bioabsorbable polymer hydrogel in vivo can be controlled by controlling the degree of the crosslinking upon production of the hydrogel.

When gelatin is used as the bioabsorbable polymer, the degree of crosslinking of the hydrogel can be evaluated using water content as a marker. The water content is weight percentage of water in the hydrogel per the weight of the swollen hydrogel. As the water content becomes greater, the degree of crosslinking of the hydrogel becomes lower, and degradation becomes faster. Water content that will exhibit a desirable sustained-release effect is about 80 to 99 w/w %, and more preferably about 95 to 98 w/w %.

When a negatively charged substance such as nucleic acid is used as the drug in the invention, it is preferred that the bioabsorbable polymer is positively charged so that a stable complex of the drug and the bioabsorbable polymer hydrogel can be formed. A stable bioabsorbable polymer hydrogel-drug complex is formed by strong binding (ionic bond) between the drug of negative charge and the bioabsorbable polymer of positive charge. To obtain a bioabsorbable polymer with a positive charge, an amino group or the like can be introduced into the bioabsorbable polymer to make it cationic. Accordingly, binding force between the bioabsorbable polymer hydrogel and the drug is enhanced, and thereby a more stable bioabsorbable polymer hydrogel complex can be formed.

The method of the cationization is not particularly limited as long as the process enables introduction of a functional group and achieves cationization under physiological conditions. Preferred is a process of introducing a primary, secondary or tertiary amino group or an ammonium group to a hydroxyl group or a carboxyl group of the bioabsorbable polymer under mild conditions. For example, alkyl diamine such as ethylenediamine or N,N-dimethyl-1,3-diaminopropane, or trimethyl ammonium acetohydrazide, spermine, spermidine, diethylamide chloride or the like is reacted with the bioabsorbable polymer using any of various condensing agents, for example, 1-ethyl-3-(3-dimethylaminopropyl)carbodiimide hydrochloride, cyanuric chloride, N,N'-carbodiimidazole, cyanogen bromide, a diepoxy compound, tosyl chloride, a dianhydride compound such as diethyltriamine-N,N,N',N'',N'''-pentanoate dianhydride, tosyl chloride or the like. Among these, a process using ethylenediamine is suitable because of convenience and versatility.

To the sustained-release preparation of the invention may be added other ingredients to achieve desired qualities, such as stability of the resulting hydrogel or persistence of release of the drug. Examples of the other ingredient include amino sugars or polymers thereof, chitosan oligomers, basic amino acids or oligomers or polymers thereof, and basic polymers such as polyallyl amine, polydiethylaminoethyl acrylamide and polyethylene imine.

The drug-containing bioabsorbable polymer hydrogel of the invention can be administered to a living body by any methods; however, topical administration is particularly preferred for allowing the drug to be released persistently at an intended particular site with directionality. The drug-containing bioabsorbable polymer hydrogel can be subjected to mixing with a pharmaceutically acceptable carrier (stabilizing agent, preservative, solubilizer, pH adjusting agent, thickening agent and the like) to prepare the sustained-release preparation, as needed. Any known carrier may be used. Furthermore, any type of additive which further regulates the sustained release effect may also be included. When formulating the sustained-release preparation of the invention, it is further desired to carry out a sterilization step such as sterilization by filtration.

The sustained-release preparation of the invention can be formulated to have any of various shapes depending on the purpose, including, for example, solid or semisolid preparation having granular, cylindrical, prismatic, sheet-like, discal, stick-like, or rod-like shape. Preferably, it is a solid preparation which is excellent in sustained release effect at the intended particular site and is suited for topical application. Additionally, it may also be used in the form of a paste preparation having fluidity. For example, the sustained-release preparation of the invention formulated to have a sheet-like shape is suited for embedding in a topical site. Also, the sustained-release preparation can be used in combination with other materials depending on the site where it is used. For example, in an attempt to fix the sustained-release preparation at a particular site, the preparation may be used after mixing with a paste substance.

The dose of the preparation of the invention may be conventionally selected such that it causes a satisfactory therapeutic response. In general, the dose may be usually selected from the range of about 0.01 to about 10,000 μg, and preferably the range of about 0.1 to about 1000 μg per one adult patient. The preparation can be embedded or infused in the lesion or a peripheral site thereof. Furthermore, when the effect is insufficient with a single dose, additional dose may be administered several times.

The sustained-release bioabsorbable polymer hydrogel preparation of the invention has both a sustained-release effect and a drug stabilizing effect, and therefore, the drug can be released at a desired site with controlled directionality for a long period of time. Accordingly, action of the drug is efficaciously exerted on the lesion.

Disclosures of all the patents and reference documents explicitly cited herein are incorporated herein by reference in their entirety. Also, disclosure of the specification and drawings of Japanese Patent Application No. 2003-71657 that is the basic application to claim priority of the present application is incorporated herein by reference in its entirety.

The present invention will be explained in detail below by way of the Examples; however, the invention is not limited by these Examples.

EXAMPLES

Example 1

Preparation of Gelatin Hydrogel Sheet

Gelatin employed was gelatin having an isoelectric point of 5.0 and a molecular weight of 100,000 which was derived from cattle bone and had been treated with alkali (Nitta Gelatin Inc., Osaka). A 5% aqueous gelatin solution was prepared, and added a predetermined amount of a 25% aqueous glutaraldehyde solution dropwise at room temperature. One ml of this aqueous solution was cast into a 2×2 cm$^2$ polytetrafluoroethylene vessel, and allowed to stand at 4° C. overnight to provide a crosslinked gelatin hydrogel. In order to remove unreacted glutaraldehyde, the gel was washed with a 100 mM aqueous glycine solution for 1 hour, and further washed twice with 50 ml of double-distilled water (DDW) for 1 hour each. After freezing at −80° C. for 3 hours, it was dried in a lyophilizer for 48 hrs to obtain a crosslinked gelatin sheet.

Measurement of water content was conducted as follows. Lyophilized hydrogel sheet was allowed to swell by immersing it in 20 ml of phosphate buffered saline (PBS, pH 7.4) at 37° C. for 24 hrs. After swelling, water on the surface of the sheet was removed using cartridge paper, and the weight (Ws) was measured. Then, the sheet was dried in a vacuum drying oven (type DN-30S, SATO VAC Inc., Tokyo) at 60° C. for 6 hrs, and the sheet weight thereafter (Wd) was measured. Water content was calculated as:

$$((W_s - W_d)/W_s) \times 100$$

Gelatin hydrogels having various water content were obtained by varying concentration of glutaraldehyde in production of the hydrogel.

| Glutaraldehyde concentration (μl/mL) | Water content in gelatin hydrogel (%) | Ws/Wd |
|---|---|---|
| 1.25 | 97.4 | 38.7 |
| 2.50 | 94.0 | 14.7 |
| 3.75 | 90.4 | 10.7 |
| 15.0 | 87.0 | 8.15 |

As a Comparative Example, a 1.5 wt % aqueous solution of poly-γ-glutamic acid (molecular weight: 60,000) was prepared, and added ethylene glycol diglycidyl ether (Nagase Chemicals, Ltd, Denacol EX-100) in an amount of 50 wt %. The mixture was left to stand at room temperature for 24 hrs to allow for a crosslinking reaction to proceed. The epoxy-crosslinked gel thus obtained was washed twice with DDW for 1 hour, and freeze-dried to provide a crosslinked poly-γ-glutamic acid hydrogel sheet. This polyglutamic acid hydrogel had a water content of 98%.

Cationized gelatin was produced as follows. Gelatin (manufactured by Nitta Gelatin Inc., derived from pig skin; molecular weight: 100,000; isoelectric point: 9) in an amount of 10 g was dissolved in 0.1 M phosphate buffer to prepare a 4% (w/w) solution. It was mixed with 27.9 g of ethylenediamine, and pH of the mixture was adjusted to 5.0 with hydrochloric acid. After adding 5.3 g of 1-ethyl-3-(3-dimethylaminopropyl)-carbodiumide, the mixture was adjusted to 500 mL with a phosphate buffer. After the reaction at 37° C. for 18 hrs, the mixture was dialyzed against ultra pure water using a cellulose tube (fractionation molecular weight: 12000-14000). Ultra pure water was exchanged 1, 2, 4, 8, 12, 24, 36 and 48 hrs after beginning of the dialysis to eliminate unreacted ethylenediamine and 1-ethyl-3-(3-dimethylaminopropyl)-carbodiimide. The thus resulting sample was freeze-dried to obtain cationized gelatin. The degree of cationization of gelatin was determined by quantitative determination of amino group of cationized gelatin by a TNBS method, demonstrating that 47% of carboxyl groups of gelatin used in the reaction were converted into amino groups.

Example 2

Preparation of CDDP-Impregnated Gelatin Hydrogel Sheet

CDDP (Nippon Kayaku Co., Ltd., Tokyo) was used as the drug incorporated in the sustained-release preparation. Using an ultrasonic homogenizer (Ultrasonic generator MODEL US150, Nisei), a 2 mg/ml aqueous CDDP solution was prepared. This aqueous CDDP solution was added dropwise to the central part of the gelatin sheet or the poly-γ-glutamic acid sheet, which was allowed to stand at room temperature for 24 hrs to impregnate CDDP into the gelatin sheet or the poly-γ-glutamic acid sheet. The amount of the aqueous solution used in this procedure was sufficient to cause swelling of the whole sheet uniformly. Thereafter, EOG sterilization was carried out at 40° C. for 24 hrs.

The thus resulting CDDP-impregnated sheet was mounted on an scanning electron microscope (SEM) sample platform with a adhesive double coated tape. After platinum coating with a vapor deposition apparatus, the sheet surface was observed with a SEM (Hitachi, Model S-450, Hitachi, Ltd., Tokyo). Conditions of SEM were: voltage of 15 kV, and magnification of 30 to 200 times. On the surface of and inside the sheet to which CDDP was added dropwise, a lot of crystals of CDDP were found on the sheet material surface. To the contrary, no CDDP crystals were found on the back face of the sheet. Every sheet was found to be similar.

Example 3

In Vitro Release Experiment

The thus resulting gelatin sheet of 2×2 cm following impregnation of the aqueous CDDP solution (water content: 97%) was placed in 10 ml of a phosphate buffer (PBS, pH 7.4) containing 0.1% Tween80, and shaken in a 37° C. incubator at 60 rpm/min. At a predetermined time, 5 ml of the supernatant was taken out. The same amount of 0.1% Tween80/PBS was immediately added to the sheet and put back in the incubator. Pt concentration in the samples was quantitatively determined three times using an atomic absorption photometer (Hitachi Model Z-8000, Hitachi, Ltd., Tokyo). The results are shown in FIG. 1. CDDP remained in the gel even after 24 hrs, suggesting that release of CDDP in the gel toward PBS by way of simple diffusion was suppressed by physicochemical interaction of CDDP with the gelatin molecule created during the impregnation process. It was found that CDDP is entirely released after approximately 3 hrs when no such interaction was created. However, release was not completely suppressed regardless of the water content, and approximately 10 to 40% of the CDDP was released. It is believed that higher water content resulted in the presence of more gelatin molecules that do not participate in crosslinkage, and therefore, CDDP was released together with uncrosslinked water soluble gelatin even under conditions in which crosslinked hydrogel is not degraded in PBS.

Figure 2:
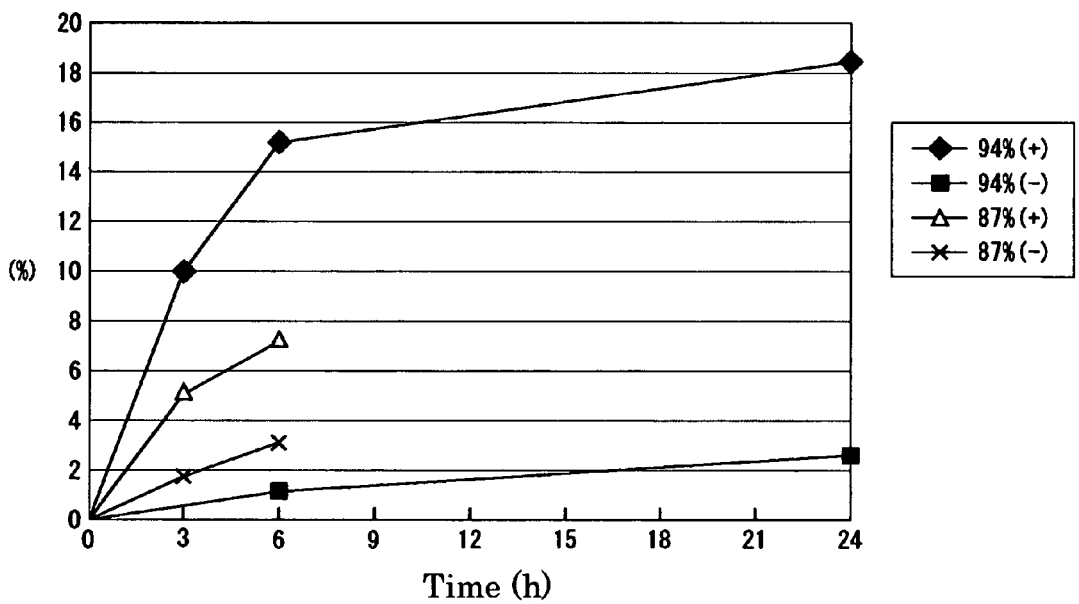
FIG. 2 is a view showing directionality of CDDP release from a CDDP-impregnated hydrogel.

Next, in order to study the difference in release from the sheet face on which CDDP was added dropwise (impregnated side) and from the unimpregnated side, a diffusion chamber model was employed. To each well of the diffusion chamber was charged 4 ml of PBS containing 0.1% Tween80, and was shaken under conditions similar to those in the aforementioned in vitro release experiment. At a predetermined time, 2 ml was taken out from each well, and to the well was immediately added the same amount of 0.1% Tween80/PBS. Quantitative determination of Pt concentration was conducted by measurement using an atomic absorption photometer in a similar manner to that described above. The results are shown in FIG. 2. In the Figure, (+) shows the side to which CDDP was added dropwise of the gelatin sheet, while (−) shows the reverse side. In either case where water content of gelatin is 94% or 87%, explicit directionality of CDDP release was found. The difference was more marked in case where water content of the gelatin sheet was 94%.

It is believed that this result was obtained because a gradient of the amount of immobilized CDDP molecules was generated in the hydrogel. More specifically, as CDDP permeates through the hydrogel, CDDP is progressively trapped through interaction with the gelatin molecules. In impregnation of the drug, this interaction is caused on the side of the sheet to which CDDP was added dropwise, thereby generating a gradient of the amount of immobilized CDDP within the sheet. However, because gelatin molecules that do not participate in crosslinkage are present within the hydrogel, CDDP interacting with this water soluble uncrosslinked gelatin is released into PBS through the aqueous phase in the hydrogel even under the in vitro condition in which hydrogel is not degraded. Directionality of the release is believed to be generated accordingly. Under conditions in which gelatin is degraded, the hydrogel is degraded uniformly, there is uniform solubilization of gelatin in water, and CDDP interacting with gelatin is released from the hydrogel. Also in this case, directionality in release is achieved.

As in the foregoing, it was revealed that direction of CDDP release can be controlled by using the CDDP-impregnated gelatin hydrogel sheet according to the invention.

Figure 3:
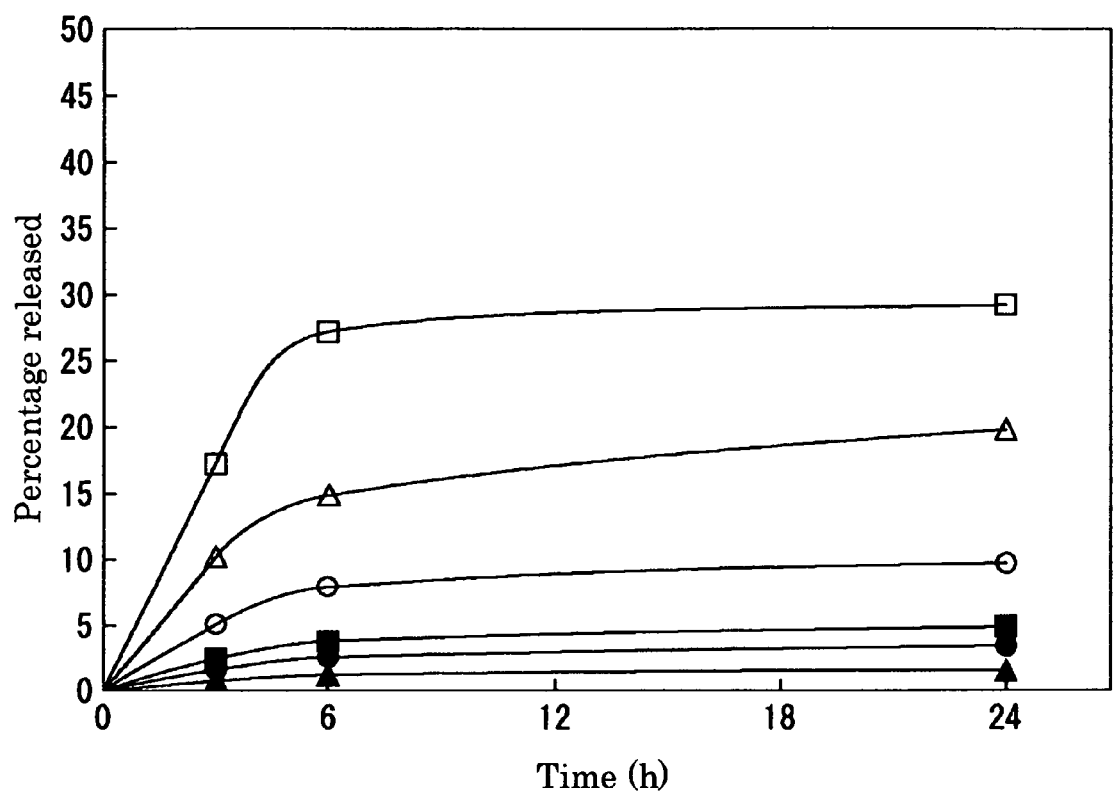
FIG. 3 is a view showing directionality of drug release from various drug-impregnated hydrogels.

Next, directionality of release of each drug from CDDP-impregnated poly-γ-glutamic acid, adriamycin-impregnated cationized gelatin and DNA oligomer-impregnated cationized gelatin sheet was investigated. The release experiment was carried out with the same method as described above. Calibration curves of concentration versus absorbance at 529 nm for adriamycin and absorbance at 260 nm for DNA oligomer were prepared, respectively, and the amount of the release was calculated therefrom. Results are shown in FIG. 3. In the Figure, open square represents adriamycin-containing gelatin (+); filled square represents adriamycin-containing gelatin (−); open triangle represents DNA oligomer-containing cationized gelatin (+); filled triangle represents DNA oligomer-containing cationized gelatin (−); open circle represents CDDP-containing poly-γ-glutamic acid (+); and filled circle represents CDDP-containing poly-γ-glutamic acid (−), where each (+) represents the side to which the drug was added dropwise, while (−) represents the reverse side thereof. Although difference in the amount of release was found to be dependent on combination of the drug and gel, clear directionality of release of the drug was found in any of the combinations of the drug and the hydrogel. Difference in amount of release depending on type of the drug is believed to result from the difference in strength of interaction between gelatin and the drug.

Example 4

In Vivo Therapeutic Experiment

Experimental animal employed was 6-weeks old female CDF1 (BALB/c×DBA/2) mouse. The animal was previously fed for 1 week. In the feeding condition, the animal was permitted to freely take solid feed and tap water in day/night cycle of 12 hours under an SPF environment over the entire period of the experiment.

MethA fibrosarcoma cells were transplanted into CDF1 mouse abdominal cavity, subcultured and maintained. The cells were suspended at $1 \times 10^7$ cells/ml, and 0.1 ml of the suspension was subcutaneously inoculated to left abdominal area of the animals. One week later, tumor volume of 45-55 $mm^3$ was ascertained, and the therapy was initiated. The experiment was carried out on the following groups (dose of CDDP (μg) is indicated in parentheses):

untreated group;
aqueous CDDP solution intraabdominally administered group (ip (80));
aqueous CDDP solution intratumorally administered group (it (20), it (40), it (80));
sheet group (S (0), S (20), S (40), S (80)).

With respect to intraabdominally administered group, the aqueous CDDP solution was prepared just before use with the aforementioned ultrasound. The solution of a total volume of 0.1 ml containing a predetermined dose of the drug was administered.

In the intratumorally administered group, a 2 mg/ml aqueous solution of CDDP was prepared just before administration with the aforementioned ultrasonic wave. Following anesthesia by intraabdominal administration of pentobarbital (10 mg/kg), the solution was administered to the central part of the tumor using a microsyringe. Administration was carried out over 30 seconds, and after fixing the syringe for another 30 seconds at the same part following administration, the syringe was drawn off.

With respect to the sheet group, four kinds of gelatin sheets with the impregnation amount of CDDP of 0, 20, 40, 80 μg were prepared as described above. The sheet of 1×1 $cm^2$ was soaked in the CDDP solution for 24 hours and freeze-dried. Water content of the gelatin sheet was 94%. Following anesthesia by intraabdominal administration of pentobarbital, a pocket was produced between the tumor and the peritoneum tissue by incising the skin in a lateral direction 1 cm below the tumor. The sheet was inserted into the pocket, and four corners were fixed by suture with a 5-0 nylon thread. Thereafter, the skin was sutured with a 5-0 nylon thread.

Measurement of the tumor diameter and body weight was carried out 3 days, 7 days, 10 days and 14 days after surgery. The tumor diameter was measured using a caliper, and the tumor volume was calculated with the formula:

$$\text{major axis} \times \text{minor axis} \times \text{thickness} \times \tfrac{1}{2}$$

Survival curve was produced with a Kaplan Meier method, and tested with a Logrank test.

Figure 4:
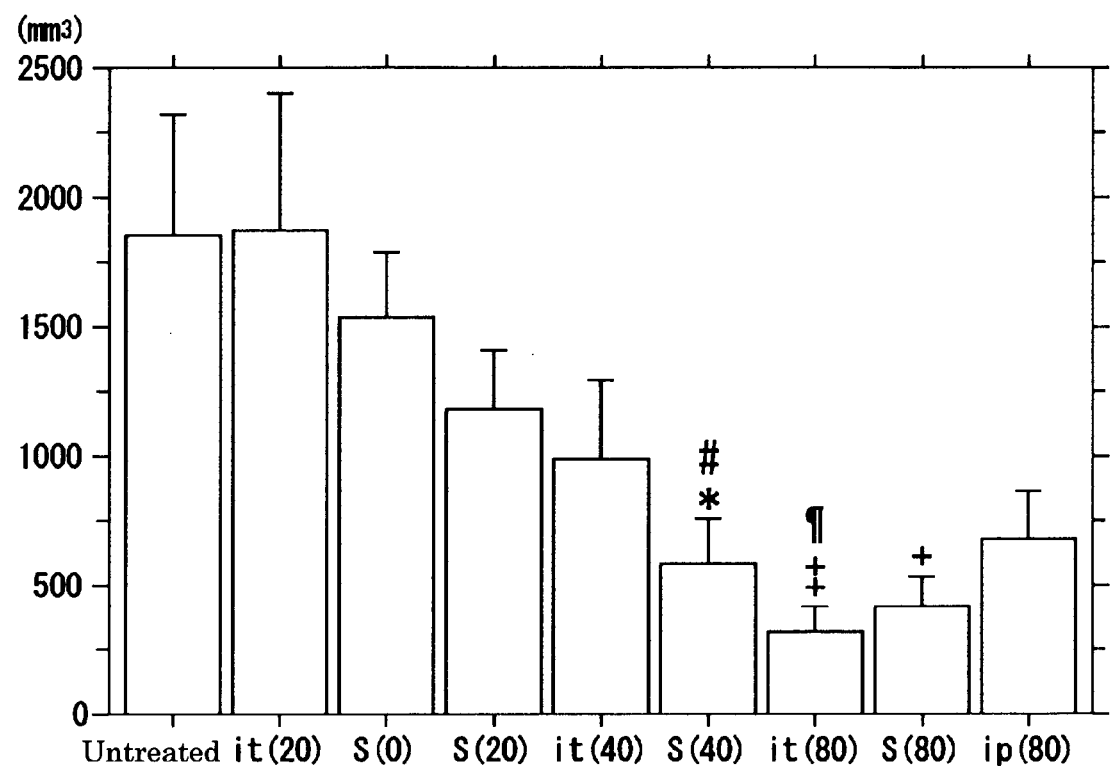
FIG. 4 is a view showing the tumor volume on Day 7 in an in vivo therapeutic experiment using a mouse.
Figure 5:
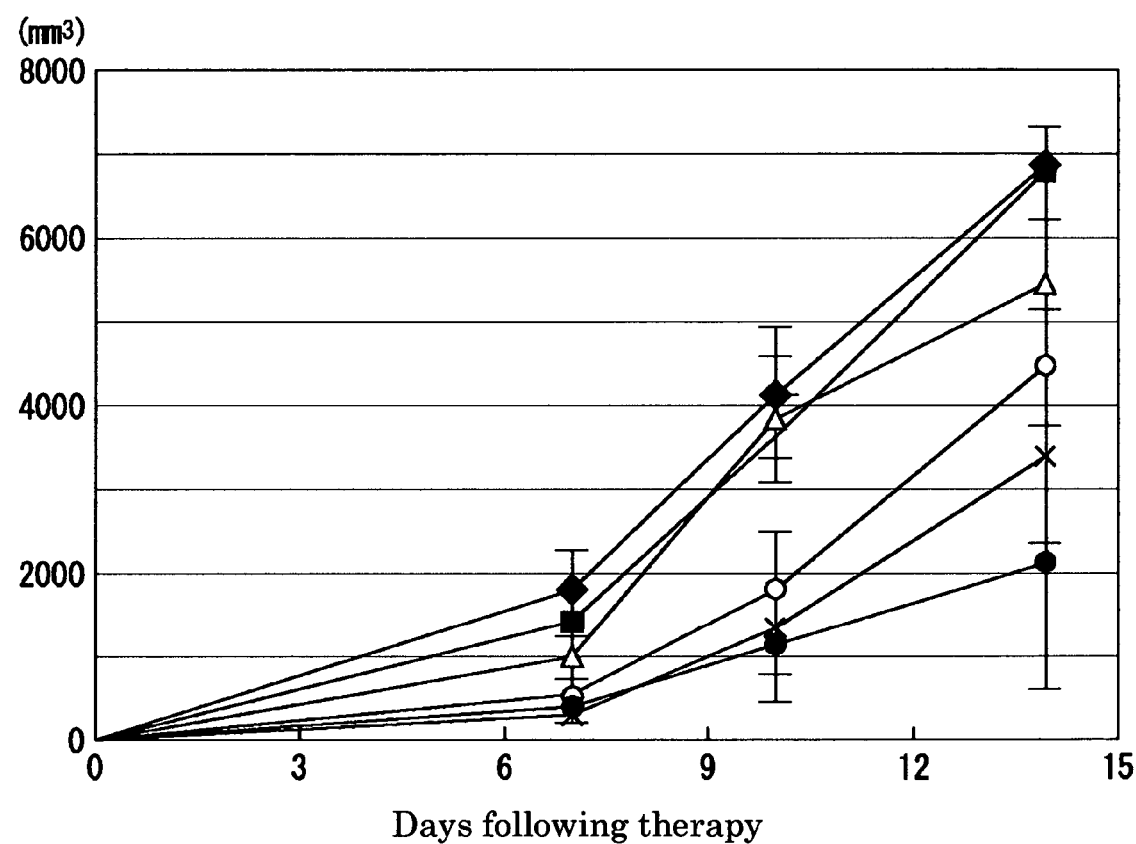
FIG. 5 is a view showing time course of the tumor volume in an in vivo therapeutic experiment using a mouse.
Figure 6:
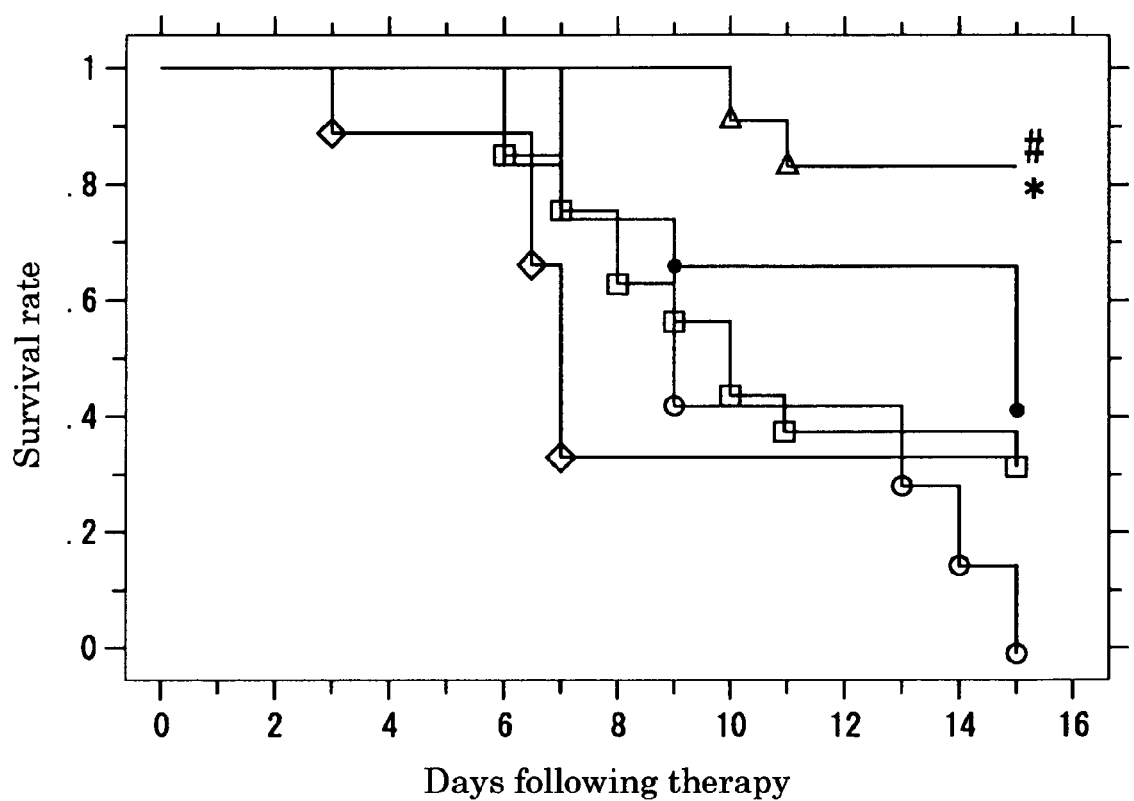
FIG. 6 is a view showing a survival curve in an in vivo therapeutic experiment using a mouse.

Tumor volume on day 7 is shown in FIG. 4. Also, time course of the tumor volume is shown in FIG. 5. In the Figures, filled diamond represents untreated group; open triangle represents it (40); open circle represents it (80); filled square represents S (0); x represents S (40); and filled circle represents S (80). Survival curves are shown in FIG. 6. In the Figure, open circle represents untreated group; open square represents it (40), open diamond represents it (80); open triangle represents S (40); and closed circle represents S (80). # indicates P<0.01 for the untreated group, it (40) and it (80). * indicates P<0.05 for S (80). It is revealed that tumor growth was significantly suppressed and survival rate was improved by using the CDDP-impregnated gelatin sheet of the invention, compared to the case where the same amount of CDDP was intraabdominally administered in an aqueous solution.

Example 5

Pharmacokinetics

Figure 7:
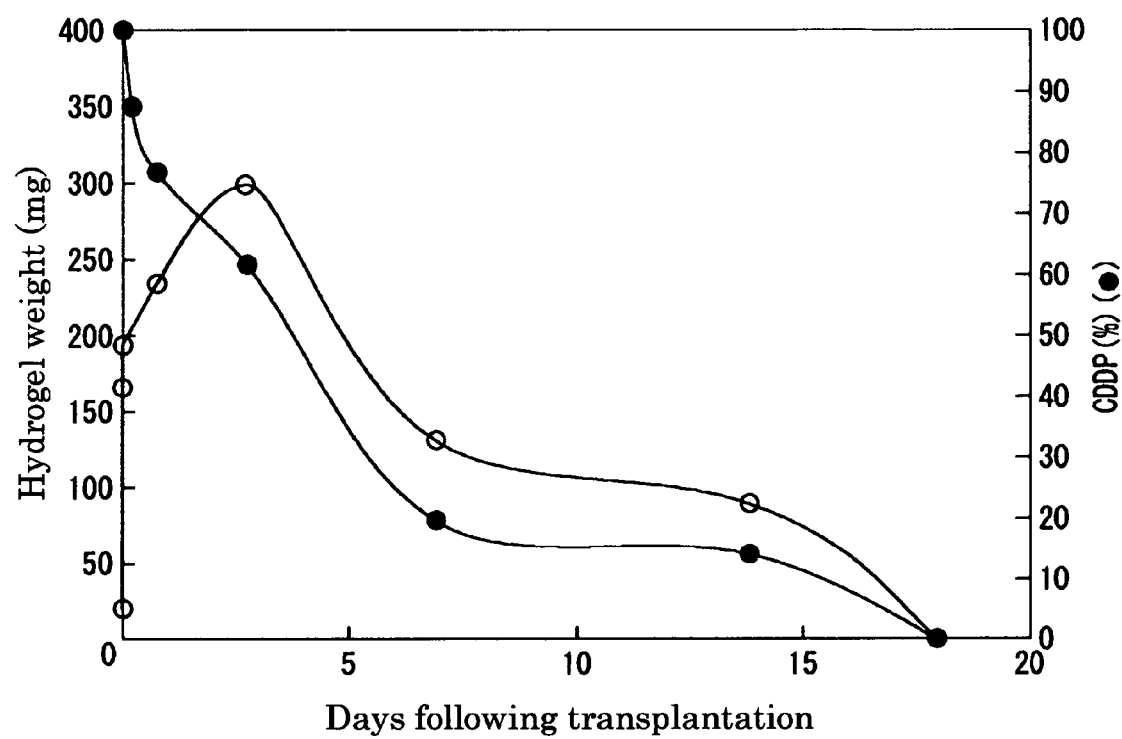
FIG. 7 is a view showing remanence of CDDP and remanence of CDDP-impregnated hydrogel under the mouse skin.

In a similar manner to Example 4, 40 μg of CDDP in a solution was intraabdominally administered, or a gelatin sheet impregnated with CDDP was administered to tumor-bearing mouse. After a predetermined time passed, the mouse was sacrificed, and the tumor tissue, and blood, kidney, liver and spleen tissues, as well as the sheet for the sheet group was quickly removed. Pt concentration in each tissue was measured with the above-referenced atomic absorption spectroscopy. Additionally, weight of the gel sheet which had been concomitantly removed was measured. Results are shown in FIG. 7. As is seen from the Figure, both Pt concentration in the tissues and the sheet weight decreased in a time dependent manner, and a significant agreement was found in the time course, suggesting that CDDP was released with degradation of the gel. It is believed that initial increase in weight of the hydrogel was caused by the embedded hydrogel being swollen with the body fluid, and the impregnated CDDP was released thereafter, due to degradation of the hydrogel by enzymatic action in vivo.

The invention claimed is:
1. A sustained-release preparation which comprises:
a drug having a molecular weight of about 10,000 or less; and
a gelatin hydrogel, wherein the drug is impregnated into said gelatin hydrogel through a surface thereof and is immobilized in said hydrogel by physiochemical interaction, and said hydrogel having a concentration gradient of the drug such that said concentration gradient being higher at said surface than in other parts of said hydrogel in said sustained-release preparation, and the drug is immobilized within said hydrogel by said physiochemical interaction, thereby controlling the directionality of the sustained release of the drug upon administration of the sustained-release preparation, and said sustained-release preparation is sterile.

2. A method of sustained release of a drug in vivo comprising:

administering a sustained-release preparation to a patient in need thereof, said preparation comprising a drug having a molecular weight of about 10,000 or less and a gelatin hydrogel, wherein said hydrogel has a concentration gradient of the drug in said sustained-release preparation, wherein degradation of the gelatin hydrogel in vivo causes more drug to be released from a region with higher drug concentration, thereby giving said sustained release of the drug, wherein the drug is impregnated into said gelatin hydrogel through a surface thereof and is immobilized in said hydrogel by physiochemical interaction, said concentration gradient being higher at said surface than in other parts of said hydrogel, and said sustained-release preparation is sterile.

3. The method of claim 2, where said administration is topical.

4. The sustained-release preparation of claim 1, wherein the drug is impregnated into said gelatin hydrogel by ionic bonding.

5. The sustained-release preparation of claim 1, wherein the preparation is in solid or semi-solid form.

6. A sustained-release preparation which comprises:

a drug having a molecular weight of about 10,000 or less; and a crosslinked gelatin hydrogel, said sustained-release preparation being made by adding an aqueous solution of said drug dropwise to said crosslinked gelatin hydrogel, thereby impregnating said drug into said crosslinked gelatin hydrogel through a surface thereof, immobilizing said drug in said crosslinked gelatin hydrogel by physiochemical interaction between said drug and crosslinked gelatin hydrogel, and forming a concentration gradient of the drug in the crosslinked gelatin hydrogel such that said concentration gradient is higher at said surface than in other parts of said hydrogel in said sustained-release preparation, wherein the amount of aqueous solution being added dropwise causes swelling of the crosslinked gelatin hydrogel and wherein said sustained-release preparation is sterile.

7. The sustained-release preparation of claim 1, in a form suitable for topical application.

8. The sustained-release preparation of claim 6, in a form suitable for topical application.

9. The sustained-release preparation of claim 1, which is in a solid or semisolid single dose form containing 0.01 to 10,000 μg of said drug.

10. The method of claim 2, wherein said sustained release preparation is in a solid or semisolid single dose form containing 0.01 to 10,000 μg of said drug.

11. The sustained-release preparation of claim 6, in a solid or semisolid single dose form containing 0.01 to 10,000 μg of said drug.

12. The sustained-release preparation of claim 1, which is in a solid single dose form containing 0.1 to 1,000 μg of said drug.

13. The method of claim 2, wherein said sustained release preparation is in a solid single dose form containing 0.1 to 1,000 μg of said drug.

14. The sustained-release preparation of claim 6, in a solid single dose form containing 0.1 to 1,000 μs of said drug.

* * * * *